United States Patent
Achter et al.

[11] Patent Number: 6,039,828
[45] Date of Patent: *Mar. 21, 2000

[54] METHOD OF FORMING A TAMPON HAVING A RESILIENT MEMBER

[75] Inventors: Amy Michele Achter, Neenah; Tammy Jo Balzar, Menasha; Donald George Fox, Neenah, all of Wis.

[73] Assignee: Kimberly-Clark Worldwide, Inc., Neenah, Wis.

[ * ] Notice: This patent is subject to a terminal disclaimer.

[21] Appl. No.: 09/035,723

[22] Filed: Mar. 5, 1998

Related U.S. Application Data

[62] Division of application No. 08/693,686, Aug. 12, 1996, Pat. No. 5,755,906.

[51] Int. Cl.$^7$ .................................................. B29C 53/00
[52] U.S. Cl. ......................... 156/217; 156/226; 156/227; 604/385.1
[58] Field of Search ...................................... 156/217, 218, 156/221, 226, 227, 554; 604/385.1, 904, 358, 378; 28/118–120

[56] References Cited

U.S. PATENT DOCUMENTS

| | | | |
|---|---|---|---|
| 1,280,979 | 10/1918 | Ellis | 604/286 |
| 2,092,427 | 9/1937 | Ross | 128/285 |
| 2,201,412 | 5/1940 | Stein | 604/904 |
| 2,264,586 | 12/1941 | Ross | 128/285 |
| 2,487,200 | 11/1949 | Trager | 128/285 |
| 2,501,972 | 3/1950 | Seidler | 128/263 |
| 2,711,173 | 6/1955 | Seidler | 128/263 |
| 2,938,519 | 5/1960 | Marco | 128/285 |
| 3,079,921 | 3/1963 | Brecht et al. | 604/904 |
| 3,138,159 | 6/1964 | Schmidt | 128/285 |
| 3,369,544 | 2/1968 | Crockford | 128/285 |
| 3,596,328 | 8/1971 | Voss | 19/144.5 |
| 3,643,661 | 2/1972 | Crockford | 128/263 |
| 3,706,311 | 12/1972 | Kokx et al. | 128/285 |
| 3,749,094 | 7/1973 | Duncan | 128/285 |
| 3,762,413 | 10/1973 | Hanke | 128/285 |
| 3,971,378 | 7/1976 | Krantz | 604/904 |
| 4,212,301 | 7/1980 | Johnson | 128/285 |
| 4,266,546 | 5/1981 | Roland et al. | 128/285 |
| 4,335,721 | 6/1982 | Matthews | 128/285 |
| 4,359,357 | 11/1982 | Friese | 156/227 |
| 4,486,191 | 12/1984 | Jacob | 604/330 |
| 5,112,348 | 5/1992 | Glassman | 604/358 |
| 5,273,521 | 12/1993 | Peiler et al. | 604/13 |
| 5,533,990 | 7/1996 | Yeo | 604/363 |
| 5,659,934 | 8/1997 | Jessup et al. | 604/904 |
| 5,755,906 | 5/1998 | Achter et al. | 156/217 |

FOREIGN PATENT DOCUMENTS

WO 95/28139  10/1995  WIPO .

*Primary Examiner*—Geoffrey L. Knable
*Attorney, Agent, or Firm*—Brinks Hofer Gilson & Lione

[57] ABSTRACT

A method of forming a catamenial tampon is disclosed wherein the tampon is useful in preventing premature leakage of body fluid from a woman's vagina and in providing better utilization of the absorbent during use. The method includes the steps of assembling a resilient member and an absorbent to form a structure having a central longitudinal axis X—X. The resilient member can be either aligned with or offset from the central longitudinal axis X—X. The absorbent and the resilient member are rolled or folded up into an elongated softwind which has a first end and a second end. The softwind is folded upon itself such that the first and second ends are aligned adjacent to one another and the softwind contains at least two folds therebetween. The softwind is then compressed into a pledget having an insertion end and a trailing end. A withdrawal string is secured to the pledget to form a tampon. The withdrawal string facilitates removal of the tampon from the woman's vagina.

11 Claims, 5 Drawing Sheets

```
┌─────────────────────────────────────────────────────────┐
│  ASSEMBLING THE ABSORBENT AND RESILIENT MEMBER          │
│                 INTO A STRUCTURE                         │
└─────────────────────────────────────────────────────────┘
                            │
┌─────────────────────────────────────────────────────────┐
│         FORMING THE STRUCTURE INTO A SOFTWIND           │
└─────────────────────────────────────────────────────────┘
                            │
       ┌──────────────────────────────────────────┐
       │       FOLDING THE SOFTWIND ON ITSELF     │
       └──────────────────────────────────────────┘
                            │
┌─────────────────────────────────────────────────────────┐
│          COMPRESSING THE SOFTWIND INTO A PLEDGET        │
└─────────────────────────────────────────────────────────┘
                            │
┌─────────────────────────────────────────────────────────┐
│      SECURING A WITHDRAWAL STRING TO THE                │
│         PLEDGET TO FORM A TAMPON                        │
└─────────────────────────────────────────────────────────┘
```

FIG. 11

METHOD OF FORMING A TAMPON HAVING A RESILIENT MEMBER

CROSS-REFERENCE TO RELATED APPLICATION

This is a division of application Ser. No. 08/693,686, filed Aug. 12, 1998, now U.S. Pat. No. 5,755,906, the contents of which are incorporated by reference.

FIELD OF THE INVENTION

This invention relates to a method of forming a tampon having a resilient member. More specifically, this invention relates to a method of forming a catamenial tampon having a resilient member which is designed to prevent premature leakage of body fluid from a woman's vagina when the tampon is initially inserted into the woman's vagina and to provide better utilization of the absorbent during use.

BACKGROUND OF THE INVENTION

Currently, there are two basic types of catamenial tampons used for feminine hygiene. The first type is a digital tampon which is designed to be inserted into a woman's vagina directly by the user's fingers. The second type is a tampon which is designed to be inserted with the aid of an applicator. Both types are usually made by folding or rolling a loosely associated strip of absorbent material into an elongated shape often referred to as a "softwind." The softwind is then radially and/or biaxially compressed into a pledget. The pledget may or may not include a cover. In both types of tampons, a withdrawal string is attached to the absorbent, either before or after compression, to facilitate removal of the tampon from the user's vagina after it has absorbed a certain quantity of body fluid, such as menses, blood, etc.

It has been found that many tampons, both digital as well as those delivered by an applicator, are unable to prevent premature leakage of body fluid. Premature leakage can result from a number of factors. One factor is that the tampon does not properly fit above the introital region of the vagina. A second factor is that the tampon has been compressed to such an extent that it is unable to open or radially expand rapidly enough after initial insertion into a woman's vagina to absorb the body fluid which comes into contact with it. A third factor is that the tampon is not shaped correctly to intercept fluid flow through the vaginal canal. A fourth factor is that the folds and convolutions of the vagina are not all in contact with the tampon and therefore body fluid is able to bypass the tampon.

Now a method of forming a catamenial tampon has been invented. The method includes forming a tampon having a resilient feature which will prevent premature leakage of body fluid immediately after being inserted into a woman's vagina and provide better utilization of the absorbent during use.

SUMMARY OF THE INVENTION

Briefly, this invention relates to a method of forming a catamenial tampon. The method includes the steps of assembling a resilient member and an absorbent to form a structure having a central longitudinal axis X—X. The resilient member can either be aligned with or offset from the central longitudinal axis X—X. The absorbent and the resilient member are then rolled or folded up into an elongated softwind which has a first end and a second end. The elongated softwind is then folded such that the first and second ends are aligned adjacent one another and the softwind contains at least two folds therebetween. The softwind is then compressed into a pledget having an insertion end and a trailing end. A withdrawal string is then secured to pledget to form a tampon. The withdrawal string facilitates removal of the tampon from a woman's vagina.

The general object of this invention is to provide a method of forming a tampon for the absorption of menses, blood, etc. A more specific object of this invention is to provide a method of forming a catamenial tampon having a resilient feature which is designed to prevent premature leakage of body fluid when initially inserted into a woman's vagina and provide better utilization of the absorbent during use.

Another object of this invention is to provide a method of forming a tampon which springs open immediately upon insertion into a woman's vagina to prevent bypass of menses and other body fluids.

A further object of this invention is to provide a method of forming a tampon which contains a resilient member which has the potential to open at least a portion of the tampon so that the tampon will contact a larger cross-section of a woman's vagina, thereby preventing the premature leakage of body fluid.

Still another object of this invention is to provide a method of forming a tampon which has wet and dry expansion capability.

Still further, an object of this invention is to provide a method of forming a tampon which exhibits reduced slippage during use.

Still further, an object of this invention is to provide a method of forming a tampon which is expandable to fit within the non-circular cross-section of a woman's vagina.

Still further, an object of this invention is to provide a method of forming a tampon with better utilization of the absorbent during use.

Other objects and advantages of the present invention will become more apparent to those skilled in the art in view of the following description and the accompanying drawings.

BRIEF DESCRIPTION OF THE DRAWINGS

FIG. 11 is a flow diagram of a method of forming a tampon.

DETAILED DESCRIPTION OF THE PREFERRED EMBODIMENTS

Figure 1:
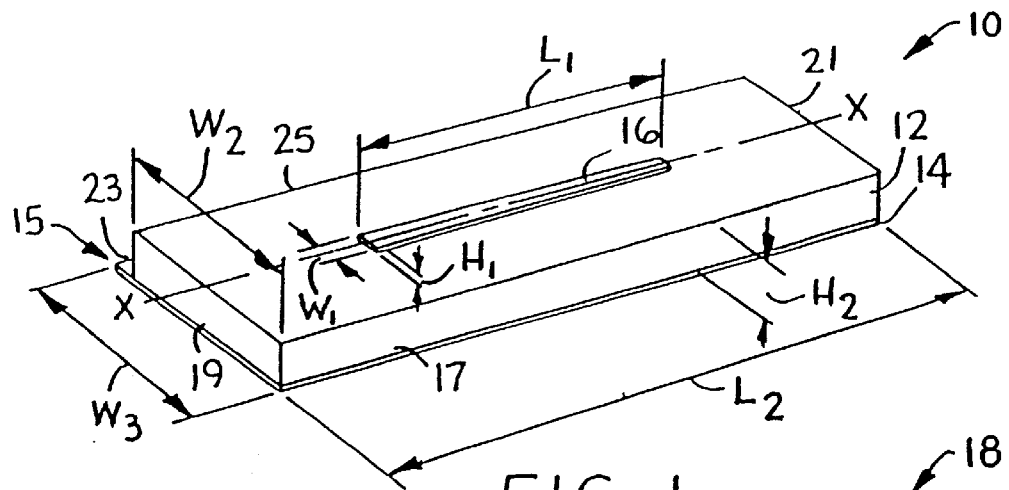
FIG. 1 is a perspective view of a resilient member positioned on an absorbent and aligned along the central longitudinal axis X—X thereof.

Referring to FIG. 1, one possible way of forming a catamenial tampon 10 is shown which is useful for absorbing body fluid from a woman's vagina, especially during her menstrual cycle. The tampon 10 is designed to be inserted above the introital region of a woman's vagina and is designed to function so as to intercept the fluid flow of menses, blood, and other body fluids and prevent the fluid from exiting the vagina. The tampon 10 includes an absorbent 12 which may contain a cover 14. The absorbent 12 can be formed from absorbent fibers which are assembled into an absorbent sheet or ribbon. Alternatively, the absorbent 12 can be formed from absorbent fibers which are assembled and compressed into a generally elongated and/or cylindrical configuration. The absorbent 12 is preferably formed from cellulosic fibers, such as cotton and rayon. The absorbent can be 100% cotton, 100% rayon, or a blend of cotton and rayon fibers. Some blends which have been tried and work well include a blend of about 15% cotton to about 85% rayon; about 70% cotton to about 30% rayon; about 60% cotton to about 40% rayon; about 25% cotton to about 75% rayon; and about 6% cotton to about 94% rayon. The particular blend of fibers can vary depending upon one's preference.

When cotton fibers are used, the cotton fibers should have a staple length of between about 5 millimeters (mm) to about 20 mm. The cotton fibers should generally have a fiber size of between about 150 microns to about 280 microns. The cotton fibers can also be bleached if desired. Bleaching will make the cotton fibers whiter in appearance.

When rayon fibers are present, the rayon fibers should have a staple length of between about 20 mm to about 35 mm. The rayon fibers should have a denier of between about 2 to about 6. Denier is a unit of fineness of yarn based on a standard of 50 milligrams (mg) for 450 meters of yarn. The rayon fibers can have a circular, a bi-lobal, a tri-lobal cross-sectional configuration, or some other cross-sectional configuration known to those skilled in the art. The bi-lobal configuration has a cross-sectional profile which looks like a dog bone while the tri-lobal configuration has a cross-sectional profile which looks like a "Y". The rayon fibers can also be bleached if desired.

The absorbent 12, when formed from an absorbent sheet or ribbon, is constructed from a blend of cotton and rayon fibers. Two processes for forming such an absorbent sheet are known as "carding" and "airlaying." Depending upon the desired absorbency one desires in the finished tampon, the basis weight of the absorbent sheet can vary. The U.S. Food and Drug Administration (FDA) has set absorbency standards for "junior", "regular", "super" and "super-plus" size tampons. In order to meet the FDA standards for these four sizes, the absorbent sheets are targeted to have basis weights of about 100 grams per square meter (gsm), 120 gsm, 170 gsm and 230 gsm, respectively. Typically, the carding process is controlled to produce an absorbent sheet with a width of between about 40 mm to about 60 mm, preferably about 50 mm. The basis weight and/or the length of the absorbent 12 can also be adjusted to form the different size tampons.

The absorbent 12 can be partially or fully enclosed by a cover 14, preferably a liquid permeable cover. By "liquid-permeable" it is meant that body fluid is able to pass through the cover 14 in a quick and efficient manner. The cover 14 can be hydrophilic or hydrophobic. By "hydrophilic" it is meant that the cover 14 has an affinity for absorbing or tending to combine with water. By "hydrophobic" it is meant the cover 14 is antagonistic to or tending not to combine with water. The cover 14 can also be treated with a surfactant or other material to make it hydrophilic or to make it more hydrophilic.

The liquid-permeable cover 14 can be formed from woven or nonwoven materials having a porous substrate. Woven materials include textile fabrics which can be made from rayon, cotton or polyolefins. The polyolefins can be either staple or continuous filaments. The nonwoven materials can include spunbond, bonded carded webs and hydroentangled webs. Spunbond and bonded carded webs are commercially sold by Kimberly-Clark Corporation having an office at 401 N. Lake Street, Neenah, Wis. 54956. Another nonwoven material which can be used as the cover 14 is formed from 100% polyester fibers held together by a binder. This material is known as powder-bonded-carded web (PBCW). PBCW is commercially available from HDK Industries, Inc. having an office at 304 Arcadia Drive, Greenville, S.C. 29609. The cover 14 can further be formed from an apertured thermoplastic film having either a two-dimensional or a three-dimensional thickness. Apertured thermoplastic films are available from several commercial vendors. Two such vendors include Pantex Srl, Pantex Sud srl, Via Terracini snc, having an office at 51031 Agliana, Pistoia, Italy and Applied Extrusion Technology having a mailing address of P.O. Box 582, Middleton, Del. 19709.

The liquid-permeable cover 14 can be treated with an aqueous solution to reduce frictional drag, to give the tampon 10 a permanent wettability and to enhance the ease of insertion into and withdrawal from a woman's vagina. The cover 14 can be treated either before being rolled or folded up with the absorbent 12 and a resilient member 16 or after a softwind 18 has been formed. The different types of aqueous solutions which can be used are known to those skilled in the art. One particular type of aqueous solution is taught in U.S. Ser. No. 08/311,692, filed Sep. 23, 1994 and entitled: "TAMPON EXHIBITING LOW FRICTIONAL DRAG." This patent application is assigned to Kimberly-Clark Corporation and is incorporated by reference and made a part hereof.

The tampon 10 further includes a resilient member 16 which is positioned on the top surface of the absorbent 12. The three vertically stacked members, from top to bottom, include the resilient member 16, the absorbent 12 and the liquid-permeable cover 14. The three members are shown having a rectangular configuration and being symmetrically aligned relative to a central longitudinal axis X—X. It should be noted that the absorbent 12 and cover 14 could have different configurations if desired, for example, an hourglass configuration. The resilient member 16 should be capable of having what is known as "dry and wet expansion" characteristics. In other words, the resilient member 16 should be made of a material which is capable of expanding back to or towards its original configuration in either a dry state, a wet state, and preferably, in both a dry and a wet state. Dry expansion of the resilient member 16 is beneficial in that the tampon 10 does not have to be wetted by body fluid before the resilient member 16 is capable of expanding. Furthermore, it is advantageous to employ a material for the resilient member 16 which is capable of expanding even while the tampon 10 is wetted by body fluid. For purposes of this invention, the resilient member 16 can be a resilient foam, such as a closed cell foam or an open cell foam. Other materials from which the resilient member 16 can be made from include polyethylene oxide (PEO) and polyvinal alcohol (PVA). The resilient member 16 can also be formed from resilient fibers such as polyolefin based fibers, polyethylene oxide fibers, hydrophobic rayon fibers and the like which preferably will have characteristics similar to those of a resilient foam. The resilient member 16 can also be made or constructed from a wettable foam. An open cell foam which works well and has good resilient properties is commercially available under the trade name ACQUELL and is sold by Sentinel Products Corporation having an office located at 70 Airport Road, Hyannis, Mass. 02601. A polyethylene closed cell foam having good flexibility characteristics also works well. This foam is commercially sold under the tradename "VOLARA" and is available from Voltex, a Division of Sekisui America Corporation, having an office located at 100 Shepard Street, Lawrence, Mass. 01843.

The resilient member 16 can have a square, rectangular, oval, circular, or any other desired cross-sectional configuration. Preferably, the resilient member 16 will have a uniform thickness and width. If desired, the dimensions of the resilient member 16 do not have to have uniform. As depicted in FIG. 1, the resilient member 16 has a length $L_1$ which is less than the length $L_2$ of the absorbent 12. The width $W_1$ of the resilient member 16 is less than the width $W_2$ of the absorbent 12. It has been found that a resilient member 16 having a length of between about 1 inch to about 5 inches (about 25.4 mm to about 127 mm), a width $W_1$ of between about 0.25 inches to about 0.50 inches (about 6.3 mm to about 12.7 mm), and a height $H_1$, of between about $\frac{1}{16}$ of an inch to about $\frac{1}{8}$ of an inch (about 1.6 mm to about 3.2 mm) works well when positioned on an absorbent 12 having a length $L_2$ of from between about 3 inches to about 10 inches (about 76 mm to about 254 mm), a width $W_2$ of from between about 1 inch to about 3 inches (about 25.4 mm to about 76 mm), and a height $H_2$ of from between about $\frac{1}{8}$ of an inch to about 1 inch (about 3.2 mm to about 25.4 mm).

Figure 3:
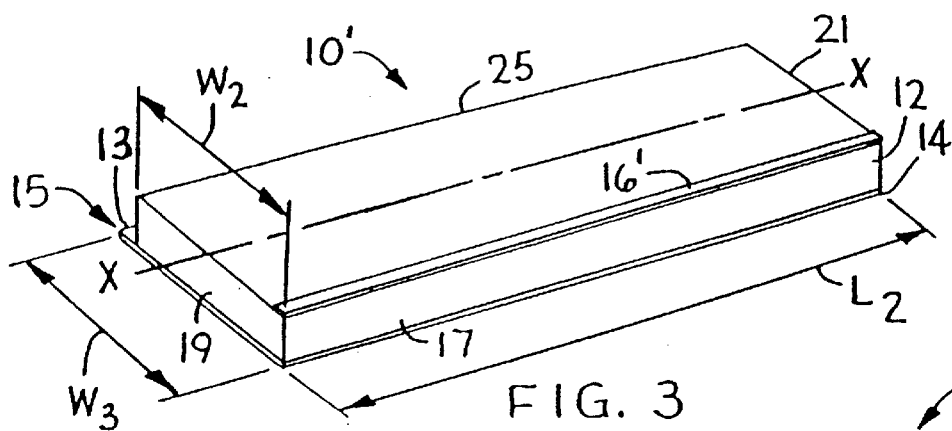
FIG. 3 is a perspective view of an alternative embodiment depicting an absorbent, cover and resilient member being aligned such that the resilient member is offset from the central longitudinal axis X—X.

The resilient member 16 can have a length $L_1$ which is only a fraction of the length $L_2$ of the absorbent 12. Alternatively, the resilient member 16 can have a length $L_1$ which is equal to the length $L_2$ of the absorbent 12. In FIG. 1, the resilient member 16 is shown having a length $L_1$ which is equal to about $\frac{1}{2}$ of the length $L_2$ of the absorbent 12. It should be noted that the resilient member 16 should have a length $L_1$ which is at least $\frac{1}{3}$ of the length $L_2$ of the absorbent ribbon 12, and preferably, at least $\frac{1}{2}$ of the length $L_2$ of the absorbent 12. Alternatively, the resilient member 16 or 16' can have a length $L_1$ which is equal to or approximately equal to the length $L_2$ of the absorbent 12, as is depicted in FIG. 3.

Figure 2:
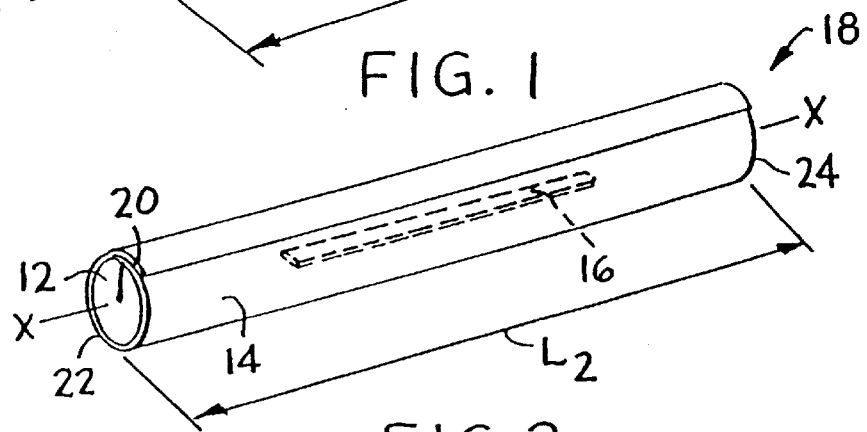
FIG. 2 is a perspective view of the absorbent and resilient member shown in FIG. 1 after being rolled or folded into a softwind.

Referring to FIG. 2, the absorbent 12, the cover 14 and the resilient member 16 are shown after they have been rolled or folded into a generally elongated member often referred to as a "softwind" 18. The softwind 18 has a central longitudinal axis X—X and is an elongated, tubular shaped member. The softwind 18 can have a circular, square, rectangular or other cross-sectional profile but preferably is elongated and has a cylindrical shape. The softwind 18 can have a length of up to about 10 inches (about 254 mm). Preferably, the softwind 18 has a length of from between about 2 inches to about 8 inches (about 51 mm to about 203 mm), and most preferably, it has a length of about 6 inches (about 152 mm). The length of the softwind can be varied so as to obtain the various size tampons.

When the softwind 18 has a circular cross-section, it can have a diameter ranging from between about 0.5 inches to about 2 inches (about 12.7 mm to about 51 mm), and preferably, will have a diameter of about 1 inch (about 25.4 mm). The specific diameter of the softwind 18 will be dictated by the type of tampon which is to be formed, such as a "junior", "regular", "super", or "super-plus" size tampon. The softwind 18 is not compressed.

When the absorbent 12, the cover 14 and the resilient member 16 are rolled into the softwind 18, the cover 14 can have a width $W_3$ which is equal to or greater than the width $W_2$ of the absorbent 12. A wider width for the cover 14 is preferred for it enables the cover 14 to be wrapped around the exterior surface of the absorbent 12 and overlap upon itself, as indicated at 20. If the width $W_3$ of the cover 14 is equal to the width $W_2$ of the absorbent 12 then the ends of the cover 14 will abut one another. The overlap design for the cover 14 is preferred.

Referring again to FIG. 2, the absorbent 12, the cover 14 and the resilient member 16 are rolled up or folded into the softwind 18 which has a first end 22 and a second end 24. The first and second ends, 22 and 24 respectively, are spaced apart from each other. Since the resilient member 16 is spaced inward from the first and second ends, 22 and 24 respectively, the resilient member 16 is not visible when the softwind 18 is formed. In forming the softwind 18, the cover 14 is depicted as being overlapped upon itself at 20 and can be bonded to itself and/or to the absorbent 12. It should be again mentioned that if the softwind 18 can be formed from the absorbent 12 alone, no cover 14 need be present. The cover 14 can be bonded using heat, pressure, heat and pressure, ultrasonics, an adhesive such as glue, or any other known bonding technique. Alternatively, the cover 14 could be sprayed onto the absorbent 12. The softwind 18 will have an length $L_2$ which will be equal to the length $L_2$ of the absorbent 12 and the cover 14. Should the cover 14 have a longer length than the absorbent 12, then the softwind 18 would have a length equal to the cover 14, unless the ends of the cover 14 are tucked at each end. The length of the cover 14 could also be less than $L_2$ to allow for cover drift during manufacture of the softwind 18.

Figure 4:
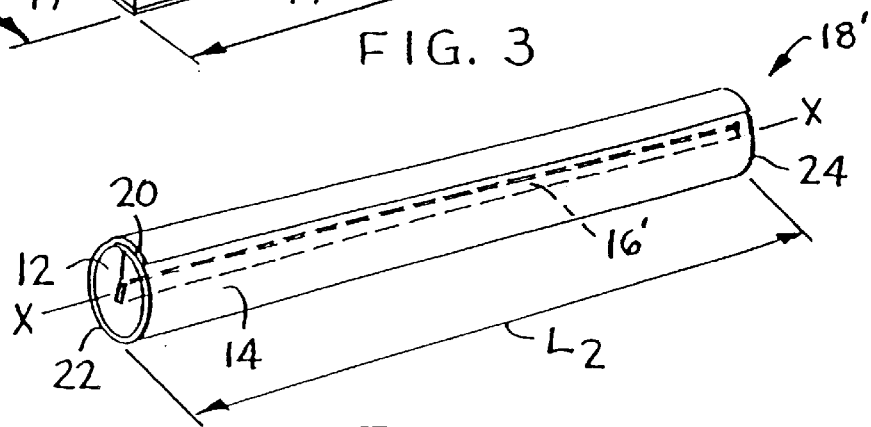
FIG. 4 is a perspective view of the absorbent, cover and resilient member shown in FIG. 3 rolled up into a softwind.

Referring to FIGS. 3 and 4, an alternative embodiment is shown wherein a tampon 10' is formed by positioning a rectangular sheet of an absorbent 12 over a rectangular sheet of a liquid-permeable cover 14 and then positioning a resilient member 16' on the upper surface of the absorbent 12. The absorbent 12 and the cover 14 both have an equal length $L_2$ which is equal to the length of the resilient member 16'. The absorbent 12 has a width $W_2$ which is slightly smaller than the width $W_3$ of the cover 14. The resilient member 16' is offset from the central longitudinal axis X—X such that it is located adjacent to an outside edge of the absorbent 12. In this configuration, it is easier to roll up the absorbent 12, the cover 14 and the resilient member 16' to form an elongated generally cylindrically shaped softwind 18'. This embodiment also shows that the resilient member 16' extends from the first end 22 to the second end 24 of the softwind 18'. In this design, the resilient member 16' is visible at each end 22 and 24 of the softwind 18'. This configuration may be advantageous in that the resilient member 16' may be able to outwardly expand the tampon 10' more fully when the tampon 10' is initially inserted into the woman's vagina. The extra length of the resilient member 16' may allow for a more positive expansion. This embodiment may also be better at preventing or reducing slippage of the tampon 10' after it has been inserted above the introital region of a woman's vagina, thereby providing superior leakage protection. Another attribute of this embodiment is that the resilient member 16' may only have to have a portion of the resilient characteristic exhibited by the shorter resilient member 16. Comfort to the consumer can thereby be enhanced by using a resilient member 16' which does not have as much strength in causing the tampon 10' to expand outward and span across the walls of a woman's vagina.

Figure 5:
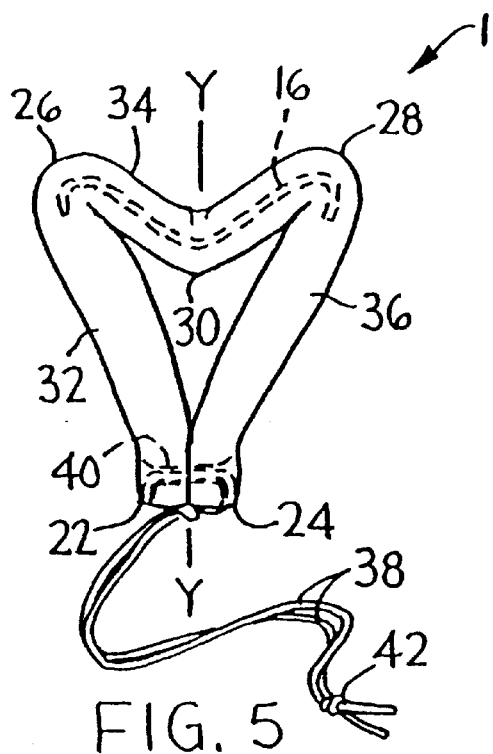
FIG. 5 is a side view of the softwind folded into a generally M-shaped profile with the first and second ends being aligned adjacent to one another and retained by the withdrawal string.

Referring to FIG. 5, the softwind 18 is folded or bent upon itself such that the first and second ends, 22 and 24 respectively, are aligned adjacent to one another and the softwind 18 contains at least two folds 26 and 28 located therebetween. By being aligned "adjacent to one another" it is meant that the first and second ends, 22 and 24 respectively, are positioned side by side, parallel to one another, offset axially or spaced radially apart from one another, or are positioned in some other type of arrangement whereby the first and second ends, 22 and 24 respectively, are close to one another. Preferably, the softwind 18 will contain three folds 26, 28 and 30 which are located between the first and second ends, 22 and 24 respectively, to give the softwind 18 a generally M-shaped profile. In the generally M-shaped profile, the softwind 18 is folded at 26 to form a first portion 32 and is folded a second time at 28 to form a second portion 34 and a third portion 36. The first and third portions, 32 and 36 respectively, preferably have approximately the same length, although their lengths can differ as desired. It is also possible to form the first, second and third portions 32, 34 and 36 to have approximately the same length. For example, if the softwind 18 has a length of about 6 inches (about 152 mm), each of the portions 32, 34 and 36 can have a length of approximately 2 inches (about 51 mm). The resilient member 16 should have a length such that it can extend between the first and second folds, 26 and 28 respectively. Preferably, the resilient member 16 will extend along the length of the second portion 34 and will have a sufficient length such that it will extend beyond the first and second folds, 26 and 28 respectively. It has been found that when the resilient member 16 extends beyond the folds 26 and 28 by at least an ⅛ of an inch (about 3.2 mm), and preferably, by at least a ¼ of an inch (about 6.4 mm), that the resilient member 16 becomes more effective in causing the second portion 34 to span laterally outward once the tampon 10 is inserted into a woman's vagina.

Referring again to FIG. 5, the third fold 30 provides the softwind 18 with the generally M-shaped profile. The third fold 30 can be positioned an equal or an unequal distance between the first and second folds, 26 and 28 respectively. When the third fold 30 is positioned an equal distance between the first and second folds, 26 and 28 respectively, the third fold 30 will be axially aligned along a central longitudinal axis Y—Y, as is shown in FIG. 5. The central longitudinal axis Y—Y vertically divides the generally M-shaped profile of the softwind 18 into left and right mirror images. It is also possible to form the third fold 30 closer to either the first or second folds, 26 and 28 respectively, if desired. The third fold 30 causes the second portion 34 of the resilient member 16 to be folded into two parts such that a V-shape is obtained for the second portion 34.

The tampon 10 further includes a withdrawal string 38 for assisting in removing the tampon 10 from the woman's vagina. The withdrawal string 38 is attached to the absorbent 12, and preferably, to the first and second ends, 22 and 24 respectively, of the softwind 18. One method of attaching the withdrawal string 38 is to form an aperture or hole 40 through the first and third portions 32 and 36, approximate the first and second ends, 22 and 24 respectively. The withdrawal string 38 is then threaded through the aperture 40 and looped upon itself so as to cinch it secure to the absorbent 12. The free ends of the withdrawal string 38 are then tied in a knot 42 to assure that the withdrawal string 38 will not separate from the softwind 18. The knot 42 also serves to prevent fraying of the withdrawal string 38 and to provide a place or point where a woman can grasp the withdrawal string 38 when she is ready to remove the tampon 10 from her vagina. It should be noted that the withdrawal string 38 holds the first and second ends, 22 and 24 respectively, in direct contact with one another and will limit the amount they can expand while positioned within the woman's vagina. It should be noted that the withdrawal string 38 can be secured to and/or attached to various areas of the softwind 18 and can pass through either the absorbent 12, the cover 14 or both. The withdrawal string 38 can also be attached either before the softwind 18 is compressed or after the softwind 18 is compressed.

The withdrawal string 38 can be constructed from various types of threads or ribbons. A thread or ribbon made from 100 percent cotton fibers works well. The withdrawal string 38 should have a length which extends beyond the end of the tampon 10 from between about 2 inches to about 8 inches (about 51 mm to about 203 mm), preferably from about 4 inches to about 6 inches (about 102 mm to 152 mm), and most preferably, about 5 inches (about 127 mm). The withdrawal string 38 can be dyed and/or treated with an anti-wicking agent, such as wax, before being secured to the softwind 18. The anti-wicking agent will facilitate and prevent body fluids from wicking along the withdrawal string 38 and contacting the inner surface of a woman's undergarment. A dry, clean withdrawal string 38 is preferred by the user, especially when she goes to remove the tampon 10 from her vagina.

Figure 6:
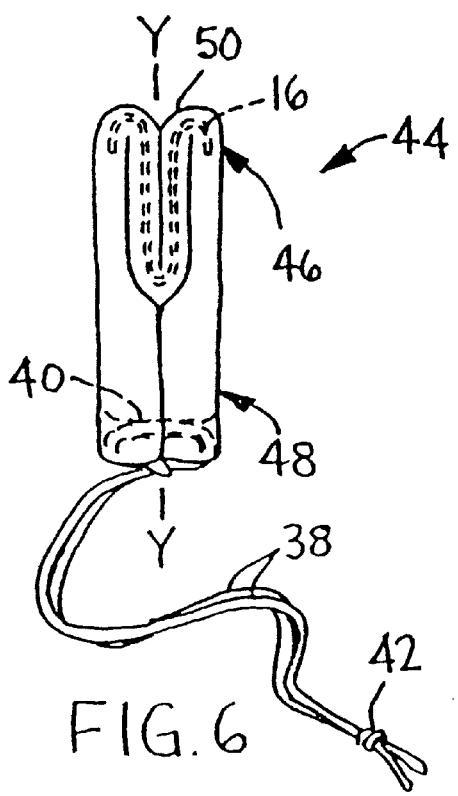
FIG. 6 is a side view of the softwind shown in FIG. 5 after it has been compressed into a piedget.

Referring to FIG. 6, the softwind 18 is compressed into a pledget 44 having an insertion end 46 and a trailing end 48. The pledget 44 can have any desired shape but preferably, it will have a generally cylindrically-shape with a circular cross-section configuration or a generally elongated shape with a rectangular cross-sectional configuration. The insertion end 46 is designed to be the first part of the pledget 44 which enters the woman's vaginal cavity. It should be noted that, while in use, the pledget 44 will be entirely positioned within the woman's vagina. The insertion end 46 contains a cleft 50 formed by the fold 30. Because the softwind 18 has a generally M-shaped profile, the insertion end 46 can contain an equal amount and, preferably, a greater amount of absorbent material than the trailing end 48. When a greater amount of absorbent material is present at the insertion end 46 and the outside diameter of the insertion end 46 is approximately equal to the outside diameter of the trailing end 48, the amount of absorbent material in the insertion end 46 will have to be densified to a greater extent than the absorbent material making up the trailing end 48. By having a greater amount of absorbent material present at the insertion end 46, the tampon 10 is better able to absorb body fluid and prevent premature leakage. When the pledget 44 is formed, the absorbent 12, the cover 14 and the resilient member 16 are all compressed. However, the compression step should not detrimentally effect the function of the resilient member 16. In other words, the resilient member 16 has to be capable of expanding outward towards or to its original configuration once the tampon 10 or 10' is inserted into the woman's vagina.

Figure 7:
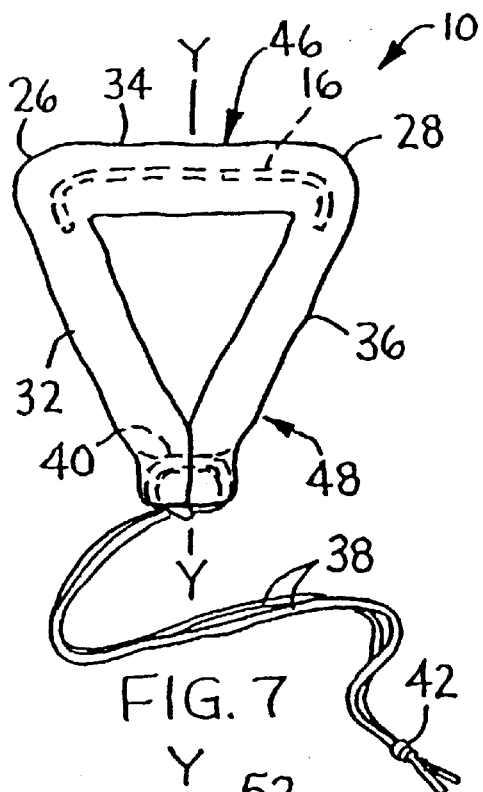
FIG. 7 is a side view of the tampon showing the configuration it attempts to acquire after it has been inserted into a woman's vagina.

Referring to FIG. 7, the tampon 10 is shown in its expanded condition which occurs immediately upon its insertion into a woman's vagina. In FIG. 7, one can see that the resilient member 16 has expanded the second portion 34 such that the third fold 30 has disappeared and the first and third portions, 32 and 36 respectively, are forced outwardly towards the interior walls of the woman's vagina. The resilient member 16 is capable of expanding laterally outward towards its original position such that at least a portion of the tampon 10 is expanded outward to intercept fluid flow through the woman's vagina. In the expanded condition, the tampon 10 will take on a generally triangular shape which is closed at the bottom or trailing end 48 by the attachment of the withdrawal string 38.

While within the vaginal cavity, the resilient member 16 will expand thereby causing the first and third portions, 32 and 36 respectively, to spring or expand outward and spread across the vaginal opening. The tampon 10 will usually be positioned below the cervix and therefore should be in a position to capture any menses, blood, and/or mucus-like clots discharged by the woman's body. The resilient, elastic and flexible characteristics of the resilient member 16 enables it to recover quickly from its compressed and deformed shape. This allows the tampon 10 to conform more ideally to the vaginal opening and press against the inside walls and convolution of a woman's vagina. This action will prevent the premature leakage of body fluid due to improper fit or the inability of the absorbent material of the tampon 10 to expand outward rapidly enough to catch any body fluid which may initially contact the tampon 10. This tampon design will also provide better utilization of the absorbent 12 during use.

The resilient member 16 also serves to reduce and/or prevent slippage of the tampon 10 within the vaginal canal. The vaginal canal is normally in a position of collapse in its lower portion for ¾ to ⅘ of its length. The lower ⅓ is essentially always closed and its inside walls are aligned side by side or next to each other as a result of the action of the muscular tissue of the vagina. As soon as the tampon 10 is inserted beyond the lower portion of the vaginal canal, the muscular tissue causes the inside walls to close off the vaginal mouth so that the tampon 10 can rest above this lower portion of the vagina. It will therefore be self-evident that the tampon 10 cannot be dislodged through movement of the wearer's body. This is an important feature of this invention.

Referring again to FIG. 7, one can see that the resilient member 16 is strong enough to cause the absorbent 12 to straighten out in the area where the third fold 30 was present. Preferably, the second portion 34 will straighten out towards its original profile and the third fold 30 will disappear upon expansion of the tampon 10 within the woman's vagina. By expanding the second portion 34 so that it bridges across the vagina opening, one can see that the tampon 10 is in a much better position to absorb the influx of menses and/or blood that may contact it after it has been inserted into the woman's vagina. It should also be recognized that by extending the length of the resilient member 16 around the locations of the first and second folds, 26 and 28 respectively, that the tampon 10 can open within the vagina while retaining a smooth curvature approximate first and second folds, 26 and 28 respectively. This smooth curvature at the locations of the first and second folds, 26 and 28 respectively, assures that the woman will not experience any discomfort during use. The presence of the resilient member 16 is also beneficial in that it does away with any required conditioning period wherein the absorbent 12 requires a certain amount of time before it can radially expand outward and intercept an appreciable amount of body fluid. Many prior art tampons are incapable of preventing leakage of body fluid until the absorbent has expanded a certain amount so as to fill the vaginal passage.

Figure 8:
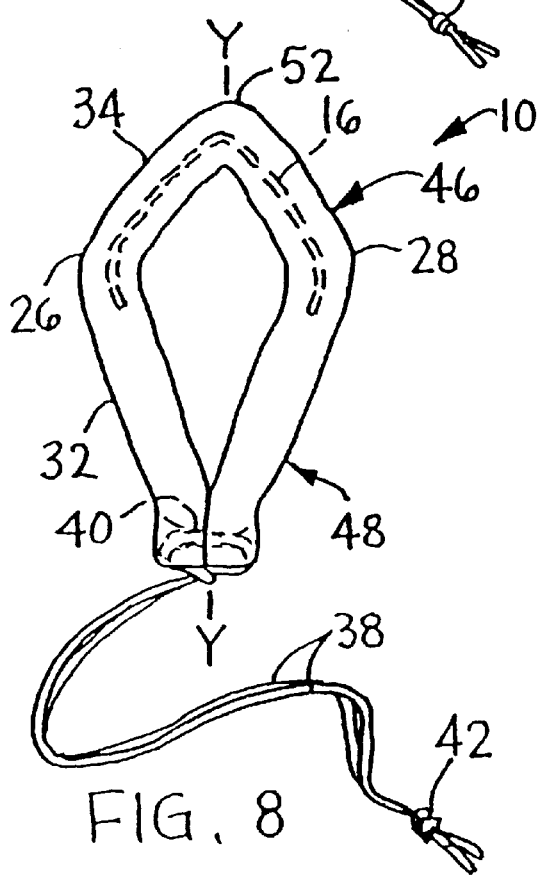
FIG. 8 is a side view of the tampon showing one possible configuration during removal from a woman's vagina.

Referring to FIG. 8, one can see that upon removal of the tampon 10 from the woman's vagina, that the second portion 34 may bow outward as the first and second folds, 26 and 28 respectively, are pressed inward by the interior walls of the woman's vagina. This action is caused by pulling downward on the withdrawal string 38. As the withdrawal string 38 is pulled downward, the first and third portions, 32 and 36 respectively, are forced inward towards one another. This action will allow the first and second folds, 26 and 28 respectively, to move closer together and will urge the second portion 34 to bow outward and form an apex 52. As this occurs, the outside diameter of the tampon 10 is significantly reduced in size and a comfortable removal of the tampon 10 is possible. It should be noted that sometimes the second portion 34 will fold inward to the configuration shown in FIG. 5 upon removal from the vagina. This configuration also allows for a comfortable removal for the first and third portions, 32 and 36 respectively, are able to move closer together as the withdrawal string 38 to pulled downward.

Figure 9:
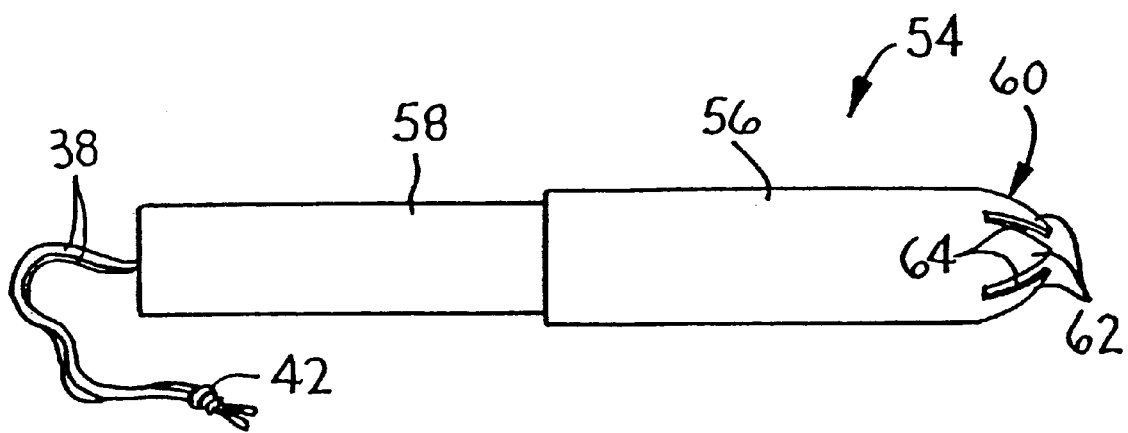
FIG. 9 is a side view of a two piece tampon applicator having an inner tube and an outer tube.
Figure 10:
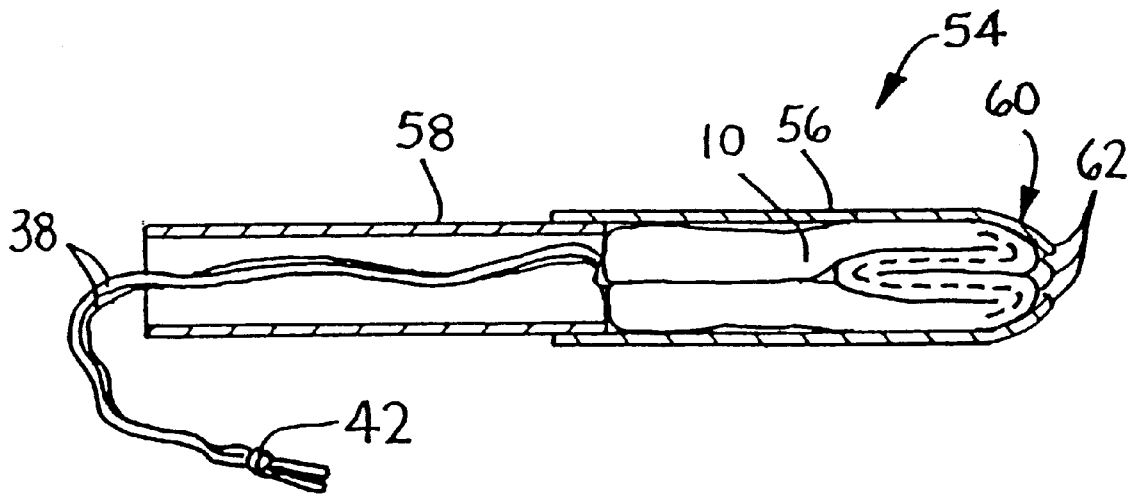
FIG. 10 is a cross-sectional view of the tampon applicator shown in FIG. 9 depicting the tampon being retained in the outer tube prior to insertion into a woman's vagina.

Referring now to FIGS. 9 and 10, a tampon applicator 54 is shown which includes an outer tube 56 and an inner tube 58. Both of the tubes 56 and 58 are hollow and each one can be formed from paper, paper board, cardboard, plastic, thermoplastic film, a combination thereof or from other known materials. The outer tube 56 and the inner tube 58 can be formed of similar or dissimilar materials, but preferably both are formed from the same material. If paper, paper board or cardboard is used, it can be coated with a wax or water-insoluble polymer to render it water-resistant. Suitable plastic materials include polyolefins, such as low density polyethylene and polypropylene. The outer tube 56 should have sufficient strength and rigidity to prevent collapsing under normal vaginal pressures. The outer tube 56 and the inner tube 58 can be formed into a cylindrical shape having a longitudinal seam or be spirally or convolutely wound. The outer tube 56 can have a relatively small diameter of between from about 10 mm to about 20 mm if desired. The inner tube 58 should be slightly smaller in diameter than the outer tube 56 and is designed to telescopically slide within the inner diameter of the outer tube 56.

The applicator 54 also has an insertion tip 60 formed at one end of the outer tube 56 which can contain a plurality of soft and flexible petals 62. The petals 62 can be arranged to form a dome-shaped nose. The petals 62 can be separated by narrow slots 64. Perforation can be substituted for the slots 64 if desired. The slots 64 allow each petal 62 to radially flex or bend outward so as to provide an enlarged opening through which the tampon 10 can be expelled as the inner tube 58 is pushed into the outer tube 56. Either an even or an odd number of petals 62 can be used, but preferably, there are an odd number of petals 62, such as 3, 5, 7, etc. By using an odd number of petals 62, one can prevent the outer tube 56 from collapsing or flattening after the tampon 10 has been expelled. Most preferably, the tampon applicator 54 will contain five petals 62. By preventing the outer tube 56 from collapsing, one can be assured that the tissues of the woman's vagina will not be pinched when the tampon applicator 54 is inserted into or removed from the woman's vagina. For optimum performance, all of the petals 62 should have the same shape and dimension. Each of the petals 62 can have an elongated, approximately truncated shape, with a rounded end and each can have a length of about ⁷⁄₁₆ of an inch (about 11.1 mm).

The tampon applicator 54 is very useful in that it will assure that the compressed tampon 10 will retain its unique shape until it is inserted into a woman's vagina. At that time, without the restriction of the outer tube 56, the resilient member 16 will be able to expand outward towards its original position such that the first and third portions, 32 and 36 respectively, will move outward towards the inner walls of the vagina.

It should be noted that even though the tampon applicator 54 has been shown as a two-piece applicator, it is possible to use a single tube applicator if desired. In a single tube applicator, only the outer tube is present and the tampon is designed to be expelled therefrom by the user's finger.

Method

The method of forming the catamenial tampon 10 and 10' will now be explained with reference to the flow diagrams shown in FIGS. 11 and 12. The method will be discussed knowing that the absorbent 12 need not be at least partially enclosed by the cover 14. The method includes the steps of assembling the resilient member 16 on the absorbent 12. By "on" is meant that the resilient member 16 is placed adjacent to or over the upper surface of the absorbent 12 such that it is vertically positioned above or situated on top of the absorbent 12. The resilient member 16 can be in physical contact with the absorbent 12 or an intermediate layer could be inserted therebetween. Preferably, the resilient member 16 will be in physical contact with the absorbent 12. The resilient member 16 and the absorbent 12 will form a structure 15 having a central longitudinal axis X—X. By "structure 15" it is meant that the resilient member 16 and the absorbent 12 can be bonded or joined together or may merely be contacting one another. Preferably, the two materials are simply arranged or vertically stacked together. However, the two materials 12 and 16 could be secured together by an adhesive, such as glue, or other known attachment means to form a laminate, if desired.

When a cover 14 is being used, the resilient member 16 is placed on the absorbent 12 such that it is spaced away from the cover 14. In other words, the resilient member 16 is positioned on the upper surface of the absorbent 12 while the cover 14 contacts the bottom surface of the absorbent 12. The resilient member 16 can be aligned along the central longitudinal axis X—X, as is shown in FIG. 1 or the resilient member 16' can be offset away from the central longitudinal axis X—X, as is shown in FIG. 3. The resilient member 16 can also be positioned closer to one end of the absorbent 12 if desired, assuming that its overall length is less than that of the absorbent 12. However, the resilient member 16 is preferably spaced an equal distance from the opposite ends of the absorbent 12.

In FIG. 1, the resilient member 16 is positioned along the central longitudinal axis X—X. The absorbent 12, the cover 14 and the resilient member 16 can be folded in half or rolled up so as to form the softwind 18. When the resilient member 16' is positioned adjacent to a longitudinal edge 17 of the absorbent 12, it makes it easier to roll up the absorbent 12, the cover 14 and the resilient member 16' to form the softwind 18'. By placing the resilient member 16' off of the centerline X—X, the resilient member 16' can be rolled up with the absorbent 12 and the cover 14 and will end up being located in the center of the softwind 18'.

Again looking at FIGS. 1 and 3, one can see that the absorbent 12 and the cover 14 both have a first longitudinal edge 17 which is coterminous or contiguous with the two layers, 12 and 14 respectively. In addition, the absorbent 12 and the cover 14 are shown having contiguous edges 19 and 21, located adjacent to the opposite ends thereof. Accordingly, the absorbent 12 and the cover 14 have three coterminous edges 17, 19 and 21. Because of this, when the softwind 18 or 18' are formed, the absorbent 12 and the cover 14 will be flush with one another at the first and second ends, 22 and 24 respectively. Furthermore, the cover 14 will have a second longitudinal edge 23 which is aligned parallel with the first longitudinal edge 17 but which is outward from another longitudinal edge 25 of the absorbent 12. The reason for this is that when the absorbent 12, the cover 14 and the resilient member 16 or 16' are rolled or folded into the softwind 18 or 18', the longitudinal edge 23 of the cover 14 can overlap upon itself and be bonded thereto. This overlap 20 is shown in FIGS. 2 and 4. It should be noted that it is not necessary to have edges 17, 19 and 21 be coterminous, nor to require that the longitudinal edge 23 of the cover 14 extend beyond the other longitudinal edge 25 of the absorbent 12. However, by sizing the absorbent 12 and the cover 14 as is shown in FIG. 1, it is advantageous to form the softwind 18 or 18'. When the absorbent 12, the cover 14 and the resilient member 16 or 16' are rolled up as shown in FIG. 4 to form the softwind 18', the cover 14 will circumferentially enclose the absorbent 12 and is overlapped upon itself at 20. At the overlap 20, the cover 14 can be bonded to itself by heat, pressure, heat and pressure, adhesive, etc.

As mentioned above, the absorbent 12, the cover 14 and the resilient member 16 can be formed into the softwind 18, as is shown in FIG. 2. In FIG. 2, the resilient member 16 is shorter in length than the length $L_2$ of the absorbent 12. Because of this length difference, the resilient member 16 will be spaced apart from the first and second ends, 22 and 24 respectively. In addition, in FIG. 2, the softwind 18 is shown being formed by folding both the absorbent 12 and the cover 14 about the resilient member 16 and then bonding the overlapped portion of the cover 20 onto itself. Alternatively, as is shown in FIGS. 3 and 4, the resilient member 16' can have a length which is equal to the length $L_2$ of the absorbent 12. In this embodiment, the absorbent 12, the cover 14 and resilient member 16' can be rolled into the softwind 18'. It should be noted that although the method has been described with respect to folding or rolling the absorbent 12, the cover 14 and the resilient member 16 or 16' to form the softwind 18 or 18', that other means may be used for forming the softwind 18 or 18'.

The softwind 18 or 18' are then folded on themselves such that the first and second ends, 22 and 24 respectively, are aligned adjacent to one another and each of the softwinds 18 or 18' contains at least two folds 26 and 28, therebetween. The two folds 26 and 28 divide the softwind 18 or 18' into a first portion 32, a second portion 34 and a third portion 36. The first, second and third portions, 32, 34 and 36 respectively, can have an equal length or they can be of different length. For example, the second portion 34 can be of a shorter length, an equal length or a greater length than the first and third portions, 32 and 36 respectively. Furthermore, it is advantageous to form three folds 26, 28 and 30 in each of the softwinds 18 or 18' which are located between the first and second ends, 22 and 24 respectively. The three folds 26, 28 and 30 will give the softwinds 18 or 18' a generally M-shaped profile, see FIG. 5. In the generally M-shaped profile, the first and second ends, 22 and 24 are held adjacent to each other and in physical contact to one another by the withdrawal string 38. After the softwind 18 or 18' has been folded into the generally M-shaped profile, the softwind 18 or 18' can be compressed to form the pledget 44, The compressed pledget 44 has an insertion end 46 and a trailing end 48.

Referring to FIG. 11, a flow diagram is depicted showing a method of forming a tampon 10 or 10'. The method includes attaching the withdrawal string to the softwind 18 or 18' after it has been compressed into the pledget 44. An aperture 40 is then formed through the trailing end of the pledget 44 or 48. The withdrawal string 38 is threaded through the aperture 40 and is looped upon itself to hold it secure to the absorbent 12. Once the withdrawal string 38 has been added, the tampon 10 or 10' is complete. The withdrawal string 38 will facilitate removal of the tampon 10 or 10' from the woman's vagina.

Figure 12:
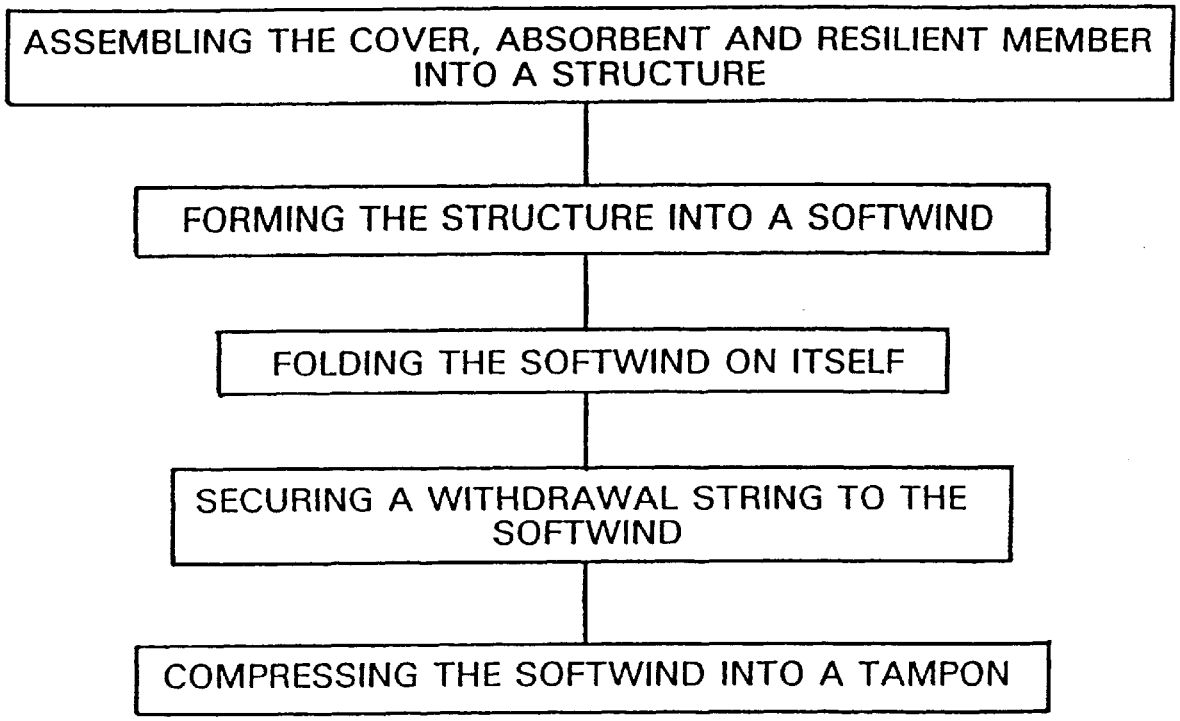
FIG. 12 is a flow diagram of an alternative method of forming a tampon.

Referring to FIG. 12, another flow diagram is depicted, which shows an alternative way to attach the withdrawal string 38. In this method, the aperture 40 is formed through the first and second ends, 22 and 24 respectively, of the softwind 18 or 18'. The withdrawal string 38 is then threaded through the aperture 40 and looped upon itself so as to secure the withdrawal string 38 to the softwind 18 or 18'. After the withdrawal string 38 has been added, the softwind 18 or 18' is compressed into the pledget 44.

It should be noted that in the above two methods, when the softwind 18 or 18' is compressed into the pledget 44, the insertion end 46 could contain more absorbent material than the trailing end 48. This additional absorbent material at the insertion end 46 is advantageous in intercepting fluid flow and preventing premature leakage of body fluid past the tampon 10 or 10' immediately after the tampon 10 or 10' has been inserted into the woman's vagina.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A method of forming a tampon, said method comprising the steps of:
   a) placing a resilient member on an absorbent to form a structure having a central longitudinal axis, said resilient member being aligned along said central longitudinal axis;
   b) forming said absorbent and resilient member into an elongated softwind having a first end and a second end;
   c) folding said softwind on itself such that said first and second ends are aligned adjacent to one another and said softwind contains at least two folds therebetween;
   d) compressing said softwind into a pledget having an insertion end and a trailing end; and
   e) securing a withdrawal string to said pledget to form a tampon, said withdrawal string facilitating removal of said tampon from a woman's vagina.

2. The method of claim 1 wherein said two folds divide said softwind into a first portion, a second portion and a third portion and said second portion is shorter in length than said first portion.

3. The method of claim 2 wherein said two folds divide said softwind into a first portion, a second portion and a third portion and said first and third portions have equal lengths.

4. The method of claim 1 wherein said softwind contains three folds located between said first and second ends.

5. The method of claim 4 wherein said softwind contains three folds giving it an M-shaped profile.

6. The method of claim 5 wherein said first and second ends of said softwind are held in contact with one another by said withdrawal string.

7. The method of claim 1 wherein said absorbent and said resilient member are rolled to form said softwind.

8. A method of forming a tampon, said method comprising the steps of:
   a) placing an absorbent on a cover to form a structure having a central longitudinal axis, said cover and said absorbent having at least one contiguous edge;
   b) placing a resilient member on said structure, said resilient member being aligned along said central longitudinal axis and being spaced apart from said cover;
   c) rolling said cover, absorbent and resilient member into an elongated softwind having a first end and a second end;
   d) folding said softwind on itself such that said first and second ends are aligned adjacent to one another and said softwind contains at least two folds therebetween;
   e) compressing said softwind into a pledget having an insertion end and a trailing end; and
   f) securing a withdrawal string to said pledget to form a tampon, said withdrawal string facilitating removal of said tampon from a woman's vagina.

9. The method of claim 8 wherein said insertion end contains more absorbent than said trailing end.

10. The method of claim 8 wherein said softwind contains three folds giving it an M-shaped profile.

11. The method of claim 8 wherein said absorbent and said cover have three coterminous edges.

* * * * *